United States Patent [19]
Fischer

[11] Patent Number: 5,957,643
[45] Date of Patent: Sep. 28, 1999

[54] FASTENING ELEMENT WITH EXPANSIBLE MEMBER

[75] Inventor: Artur Fischer, Waldachtal, Germany

[73] Assignee: fischerwerke Artur Fischer, Waldachtal, Germany

[21] Appl. No.: 08/948,115

[22] Filed: Oct. 9, 1997

[30] Foreign Application Priority Data

Oct. 12, 1996 [DE] Germany .......................... 196 42 201
Dec. 12, 1996 [DE] Germany .......................... 196 51 687

[51] Int. Cl.⁶ ................................................. F16B 13/04
[52] U.S. Cl. ............................. 411/78; 411/76; 411/903
[58] Field of Search ....................... 411/76, 77, 78, 411/79, 80, 902, 903, 913

[56] References Cited

U.S. PATENT DOCUMENTS

| | | |
|---|---|---|
| 2,287,395 | 6/1942 | Reynolds . |
| 3,117,483 | 1/1964 | Brown ....................................... 411/76 |
| 3,342,097 | 9/1967 | Rocheleau ................................. 411/76 |
| 3,844,194 | 10/1974 | Reinwall, Jr. . |
| 5,562,376 | 10/1996 | Fischer ............................... 411/903 X |
| 5,741,100 | 4/1998 | Fischer ............................... 411/903 X |

FOREIGN PATENT DOCUMENTS

| | | |
|---|---|---|
| 29 14 739 | 10/1980 | Germany . |
| 44 33 918 A1 | 10/1995 | Germany . |
| 44 23 234 A1 | 1/1996 | Germany . |
| 195 36 786 A1 | 10/1996 | Germany . |
| 175127 | 2/1922 | United Kingdom . |
| 831740 | 3/1960 | United Kingdom . |

*Primary Examiner*—Neill Wilson
*Attorney, Agent, or Firm*—Michael J. Striker

[57] ABSTRACT

A fastening element has a shaft having a rear end and a forward end with a forward end face, holding means arranged at the rear end of the body for fastening an article to a building component, means forming an expansible region starting from the forward end face and extending in a longitudinal direction through a portion of a length of the shaft, the means forming the expansible region including a longitudinal slot having a base and an expansible member seated displaceably on the base of the longitudinal slot, the expansible member being provided with a stop which abuts the forward end face of the shaft.

11 Claims, 2 Drawing Sheets

FASTENING ELEMENT WITH EXPANSIBLE MEMBER

BACKGROUND OF THE INVENTION

The present invention relates to a fastening element with an expansible member.

More particularly, it relates to a fastening element having a holding means arranged at the rear end for the purpose of fastening an article to a building component.

DE 44 33 918 A1 discloses a fastening element, which has, in the region of its forward end face, an expansible region formed by a longitudinal slot and an expansible element seated displaceably on the base of the longitudinal slot. The expansible element lies on the base of the longitudinal slot which has rises towards the forward end face. The outward face of the expansible member projects radially beyond the shaft of the fastening element and is provided with teeth. If, once the fastening element has been anchored, a drilled hole becomes enlarged through the formation of cracks, the shaft of the fastening element is displaced, by a tensile load acting on it with respect to the expansible member firmly seated in the wall of the drilled hole. As a result the enlargement of the drilled hole is compensated by means of the base of the longitudinal slot, which rises towards the forward end face. The known fastening element is therefore suitable for use in the tension zone, in which drilled holes may become enlarged through the formation of cracks.

When the known fastening element is driven into a drilled hole in a building component, the expansible member must, in order to avoid premature expansion, be supported against the shaft of the fastening element. For that purpose, the boundary of the longitudinal slot facing towards the rear end face of the fastening element is constructed as a stop surface transverse to the longitudinal axis. As a result, on the one hand a resource-intensive production process is required for making the longitudinal slot in the shaft. On the other hand the shaft of the fastening element is weakened in the region of the stop surface as a result of notching and the depth of the longitudinal slot in question, which weakening result in a reduction of the holding value of the known fastening element. Furthermore, when the fastening element is driven in, bore dust is scraped off the walls of the drilled hole by the forward end edge of the expansible member located within the longitudinal slot. The bore dust penetrates into the longitudinal slot and can jam the expansible member in the longitudinal slot in such a manner that displaceability and, as a consequence, further expansion can no longer be ensured or are impaired in the event of a drilled hole's becoming enlarged through the formation of cracks.

SUMMARY OF THE INVENTION

Accordingly, it is an object of the present invention to provide a fastening element with an expansible member which eliminates the disadvantages of the prior art.

More particularly it is an object of present invention to provide a fastening element with an expansible member, which is improved in such a manner that it can be manufactured more simply and more economically, and reliable further expansion is achieved in the event of a drilled hole's becoming enlarged through the formation of cracks.

In keeping with these objects and with others which will become apparent hereinafter, one feature of the present invention resides, briefly stated, in a fastening element having a holding means arranged at a rear end for fastening an article to a building component and having an expansible region starting from the forward end phase and extending in the longitudinal direction through a portion of the length of its shaft with the expansible region formed by a longitudinal slot and an expansible element seated displaceably on the base of the longitudinal slot, wherein in accordance with the present invention the expansible element has a stop which abuts against the forward end face of the fastening element.

When the fastening element is designed in accordance with the present invention, it avoids the disadvantages of the prior art and provides for the highly advantageous results.

Because the terminal portion both of the base of the longitudinal slot and of the contact surface of the expansible member are arcuate, edges are avoided which could hinder the sliding of the expansible member. The longitudinal slot may now be made advantageously by means of a disk-shaped milling cutter, the radius of which corresponds to the radius of the terminal portion.

In accordance with the present invention, in order to prevent the expansible member from being displaced in the direction towards the rear end face when the fastening element is being driven into the drilled hole and, as a result, from causing premature expansion, the expansible member has a stop, which abuts the forward end face of the fastening element. As a result of that construction, the scraping edge lies outside the longitudinal slot. Thereby when the fastening element is driven in, no bore dust or only small amounts of bore dust, which could wedge the expansible member in the longitudinal slot, penetrate(s) into the longitudinal slot. As a result of supporting of the expansible member by the stop abutting the forward end face of the fastening element, there is also avoided compression of the expansible when it is being driven into the drilled hole, which would cause a higher resistance to driving in.

In accordance with a further feature of present invention, in order that the expansible member is better able to grip the walls of the drilled hole, the outward face of the expansible member can be provided with teeth, which project radially beyond the shaft.

In the present invention the expansible member can be retained in the longitudinal slot by means of a displaceable holding element, for example a plastic clip, in order to avoid the expansible member unintentionally falling out of the longitudinal slot. With its two limbs, the plastic cup grips slightly around the semi-circular cross-section of the shaft in such a manner that the limbs provide the holding function for the expansible member. In order to prevent the holding element from twisting on the shaft, in a further development a longitudinal groove embracing the expansible member is arranged in the zenith of the plastics clip and on its internal surface.

In order to ensure that the expansible member can be displaced readily even under extreme conditions, a sliding means can be provided on the base of the longitudinal slot and/or on the contact surface of the expansible member.

The expansible element can be coated with a harder material than the shaft. As a result, good sliding characteristics are obtained.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
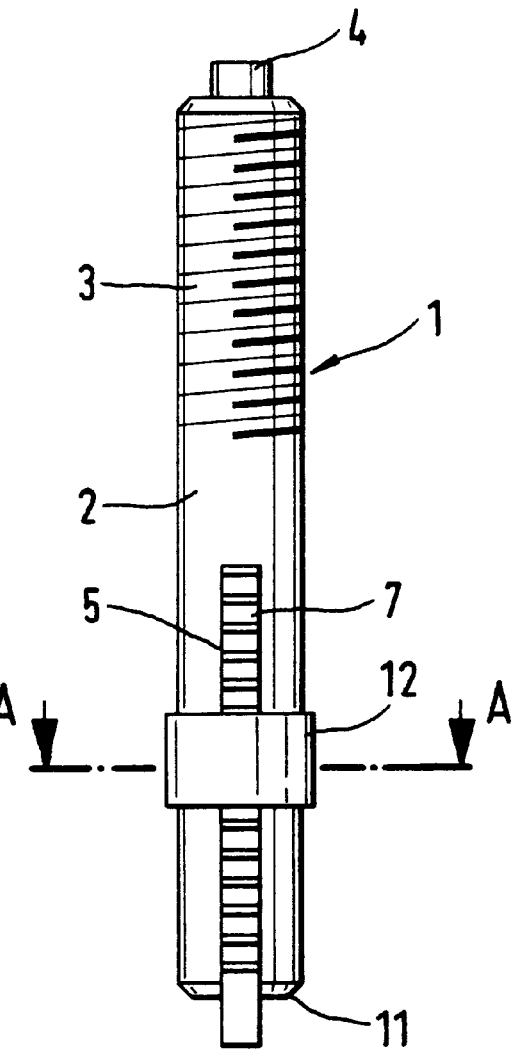
FIG. 1 shows a fastening element of the present invention having an expansible member lying in a longitudinal slot.
Figure 2:
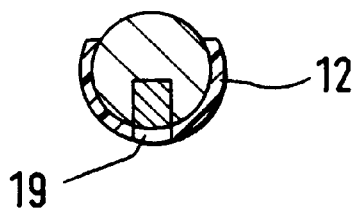
FIG. 2 shows a cross-section through the fastening element of the present invention in the region of the holding element corresponding to the section line A—A.
Figure 3:
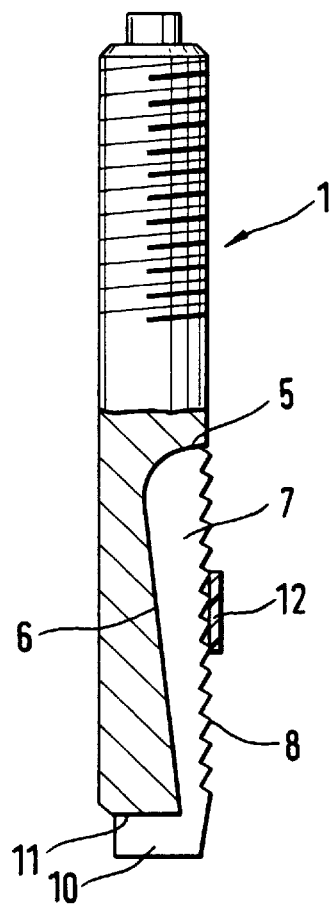
FIG. 3 shows a partial longitudinal section through the fastening element of the present invention of FIG. 1.

A fastening element 1 in accordance with the present invention illustrated in FIGS. 1 to 3 has a shaft 2 having an external thread 3 at the rear end 4 and an expansible region, which is formed by a longitudinal slot 5 and an expansible member 7 lying in that longitudinal slot. The base 6 of the longitudinal slot 5 and the contact surface of the expansible member 7 is in the shape of a hook for the purpose of forming the stop 10 and abuts the forward end face 11 of the fastening element 1. The expansible member 7, which lies in the longitudinal slot 5, is held by a displaceable holding element 12. The holding element 12 is constituted by a plastic clip. Its limbs grip further around the shaft 2 of the fastening element than a semi-circular cross-section. For the purpose of locking the clip against twisting, the clip has a longitudinal groove 19 embracing the projecting portion of the expansible element 7.

The expansible member 7 has, on its outward face, sawtooth-shaped teeth 8. The teeth 8 project beyond the shaft 2 by approximately the tooth height. A sliding means can be provided on the base 6 of the longitudinal slot 5 and/or on the contact surface of the expansible member 7, and formed for example a coating with high sliding properties. The sliding means ensures that the expansible member 7 and the shaft 2 of the fastening element 1 are displaceable relative to one another even under extreme conditions. Advantageous sliding characteristics can also be obtained when the expansible member 7 consists of a material, for example steel, that is harder than the shaft 2.

Figure 4:
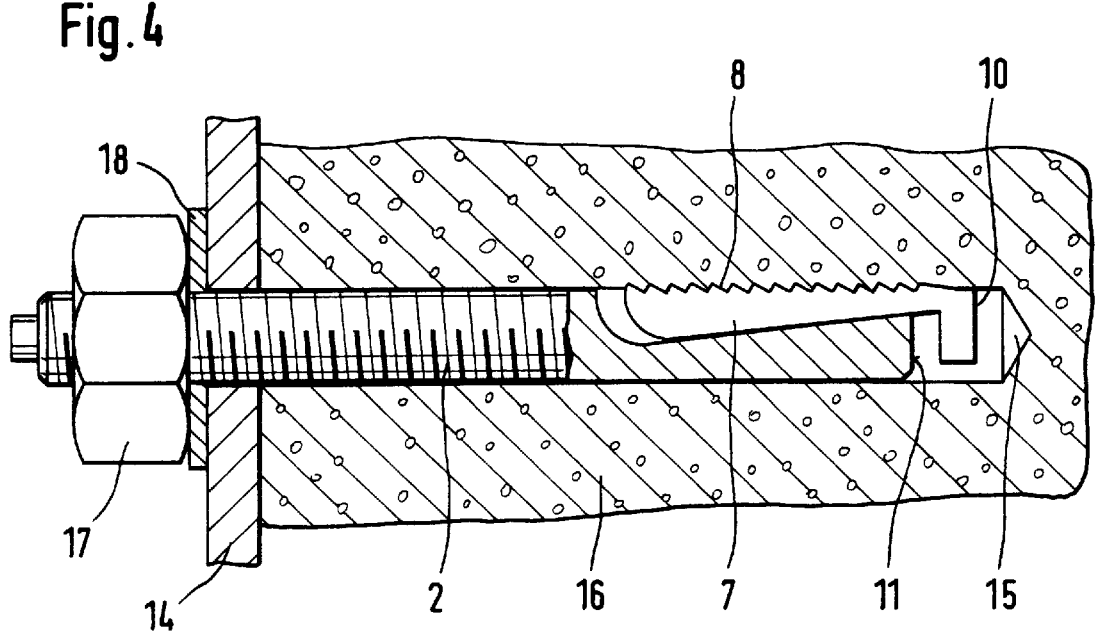
FIG. 4 shows the fastening element of the present invention anchored in the drilled hole.

FIG. 4 shows the fastening element in accordance with the present invention anchored in a drilled hole 15 in a building component. A nut 17 has been screwed onto the thread 3 of which fastening element for fastening the article 14. A washer 18 is arranged under the nut 17. Screwing on the nut causes a tensile force to act on the fastening element 1. The tensile force wedges the expansible member 7 together with the shaft 2 in the drilled hole as a result of the axial displacement occurring in that process. An axial displacement having the same effect is also produced when a drilled hole becomes enlarged through the formation of cracks. As a result of the increasing radial wedging of the expansible member, the enlargement of the drilled hole is compensated.

It will be understood that each of the elements described above, or two or more together, may also find a useful application in other types of constructions differing from the types described above.

While the invention has been illustrated and described as embodied in fastening member with expansible member, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A fastening element, comprising a shaft having a rear end and a forward end with a forward end face; holding means arranged at said rear end of said body for fastening an article to a building component; means forming an expansible region starting from said forward end face and extending in a longitudinal direction through a portion of a length of said shaft, said means forming said expansible region including a longitudinal slot having a base and an expansible member seated displaceably on said base of said longitudinal slot, said expansible member being provided with a stop which abuts said forward end face of said shaft.

2. A fastening element as defined in claim 1, wherein said stop of said expansible member is formed as a hook.

3. A fastening element as defined in claim 1, wherein said expansible member has an outward face provided with teeth which project radially beyond said shaft.

4. A fastening element as defined in claim 1; and further comprising displaceable holding means which act on said expansible member so as to retained said expansible member on said longitudinal slot.

5. A fastening element as defined in claim 4, wherein said holding means include a holding element formed as a clip with limbs which grip around said shaft further than a semi-circular cross-section of said shaft.

6. A fastening element as defined in claim 5, wherein said clip of said holding means is formed as a plastic clip.

7. A fastening element as defined in claim 5, wherein said clip has a longitudinal groove provided in a zenith and on an internal surface of said clip, said longitudinal slot embracing said expansible member.

8. A fastening element as defined in claim 1; and further comprising sliding means provided on a base of said longitudinal slot.

9. A fastening element as defined in claim 1; and further comprising sliding means provided on a surface of said expansible member which is in contact with said base of said longitudinal slot.

10. A fastening element as defined in claim 1; and further comprising sliding means provided on said base of said longitudinal slot which is in contact with surface of said expansible member.

11. A fastening element as defined in claim 1, wherein said expansible member is composed of a material which is harder than a material of said shaft.

\* \* \* \* \*